US00PP11220P

United States Patent [19]

Zary

[11] Patent Number: Plant 11,220

[45] Date of Patent: Feb. 15, 2000

[54] FLORIBUNDA ROSE PLANT NAMED 'JACTAFL'

[75] Inventor: Keith W. Zary, Thousand Oaks, Calif.

[73] Assignee: Bear Creek Gardens, Inc., Medford, Oreg.

[21] Appl. No.: 09/001,569

[22] Filed: Dec. 31, 1997

[51] Int. Cl.[7] ..... A01H 5/00

[52] U.S. Cl. ..... Plt./148

[58] Field of Search ..... Plt./148, 137, 107, Plt./141, 143

*Primary Examiner*—Howard J. Locker

*Attorney, Agent, or Firm*—Klarquist Sparkman Campbell Leigh & Whinston, LLP

[57] ABSTRACT

A floribunda rose plant having a very vigorous growth habit; high centered flowers presented in large clusters and disease resistant foliage.

1 Drawing Sheet

The present invention relates to a new and distinct variety of rose plant of the floribunda class which was originated by me by crossing an unnamed seedling, with the variety 'JACjem,' U.S. Plant Pat. No. 5,001.

The primary objective of this breeding was to produce a new rose variety having the tall, vigorous growth, high petal count and high centered form of the unnamed pink floribunda female parent combined with the glossy, disease resistant foliage of the male parent. The objective was substantially achieved, along with other desirable improvements, as evidenced by the following unique combination of characteristics that are outstanding in the new variety and that distinguish it from its parents, as well as from all other varieties of which I am aware:

1. Glossy, disease resistant foliage;
2. High centered flower form;
3. Very vigorous, very upright growth habit;
4. Flowers presented in large clusters.

'JACtafl' is a tall growing floribunda reaching over four feet tall in one season of growth. Its growth habit is very upright—almost columnar. Flowers are presented at the top of the plant.

Asexual reproduction of this new variety by budding, as performed at Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—JACjem (U.S. Plant Pat. No. 5,001).

Classification:

*Botanical.*—Rosa hybrida.

*Commercial.*—Floribunda.

FLOWER

Observations made from specimens grown in a garden environment at Somis, Calif. from January, 1996–February, 1997.

Blooming habit: Recurrent.

Bud:

*Size.*—One and one-half inches long when the petals start to unfurl.

*Form.*—The bud form is long, pointed ovoid.

*Color.*—When sepals first divide, bud color is Red Group 49C, edged in Red Group 45D. When half blown, the upper sides of the petals are Red Group 49B on petal edges and Red Group 49C over the rest of the petal; and the lower sides of the petals are Red Group 49B on the petal edges and Red Group 49D over the rest of the petal.

*Sepals.*—Color: Green group 138B. Surface texture: Covered with fine hairs. There are three normally appendaged sepals. There are two unappendaged sepals with hairy edges.

*Receptacle.*—Color: Green Group 137B. Shape: Funnel. Size: Medium (5/16" long×3/16" wide). Surface: Smooth.

*Peduncle.*—Length: Medium (2½" to 3"). Surface: Glandular. Color: Medium green and bronzy. Strength: Stiff, erect.

Bloom:

*Size.*—Medium. Average open size is 3½ to 4 inches.

*Borne.*—Several together in flat clusters of three to nine flowers.

*Stems.*—Long, (16–20").

*Form.*—When first open: High centered Permanence: Retains its form to the end, outer petals curl back.

*Petalage.*—Number of petals under normal conditions: 25–30.

*Color.*—The upper sides of the petals are Red Group 49B on petal edges and Red Group 49C on the rest of the petal. The reverse sides of the petals are Red Group 49B on the petal edges and Red Group 49D over the rest of the petal. The base of each petal has a small (3/16"×3/16") yellow half-moon at the point of attachment. The major color on the upper side is Red Group 49C.

*Variegations.*—Occasional greenish streaks on the guard petals.

*Discoloration.*—At the end of the first day: No change. At the end of the third day: No change. By day four or five there is fading of the pink color to Red Group 49C on the petal edges and Red Group 49D on the rest of the petal.

*Fragrance.*—Slight.

Petals:

*Texture.*—Thick.

*Shape.*—Round.

*Form.*—Tips slightly recurved.

*Arrangement.*—Imbricated. Petaloids in the center are few.

*Persistence.*—Drop off cleanly.

*Lastingness.*—On the plant: Fair (five or six days). As a cut flower: Not tested.

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles.*—Color: Red.

*Stigmas.*—Color: Greenish-white.

Plant:

*Form.*—Bush.

*Growth.*—Very vigorous; upright; branching; Height after one full season of growth in Somis, Calif. is 4 to 4½' tall by 3' wide.

*Foliage.*—Number of leaflets on normal mid-stem leaves: Five or seven.

*Size.*—Large.

*Quantity.*—Abundant.

*Color.*—New foliage: Upper surface: Greyed-Orange 176A; Lower surface: Greyed-Orange 176C. Old foliage: Upper surface: Green Group 139A. Lower surface: Green Group 139C. New foliage quickly turns green beginning on upper surface shortly after leaf unfolds.

*Shape.*—Pointed oval.

*Texture.*—Upper side: Glossy.

*Edge.*—Serrated.

*Serration.*—Single, small.

*Petiole rachis.*—Color: Green.

*Petiole underside.*—Smooth with occasional prickles.

*Stipules.*—Medium (⅝" long); serrated, bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Many. On laterals from main canes: Many.

*Form.*—Medium (¼"); hooked downward.

*Color when young.*—Red.

Small prickles:

*Quantity.*—On main stalks: Many. On laterals: Many.

*Color.*—Green but turn brown with age.

I claim:

1. A new and distinct variety of rose plant of the floribunda class, substantially as herein shown and described, characterized particularly as to novelty by its very vigorous upright growth habit; high centered flower form; glossy, disease resistant foliage; and flowers presented in large clusters.

* * * * *

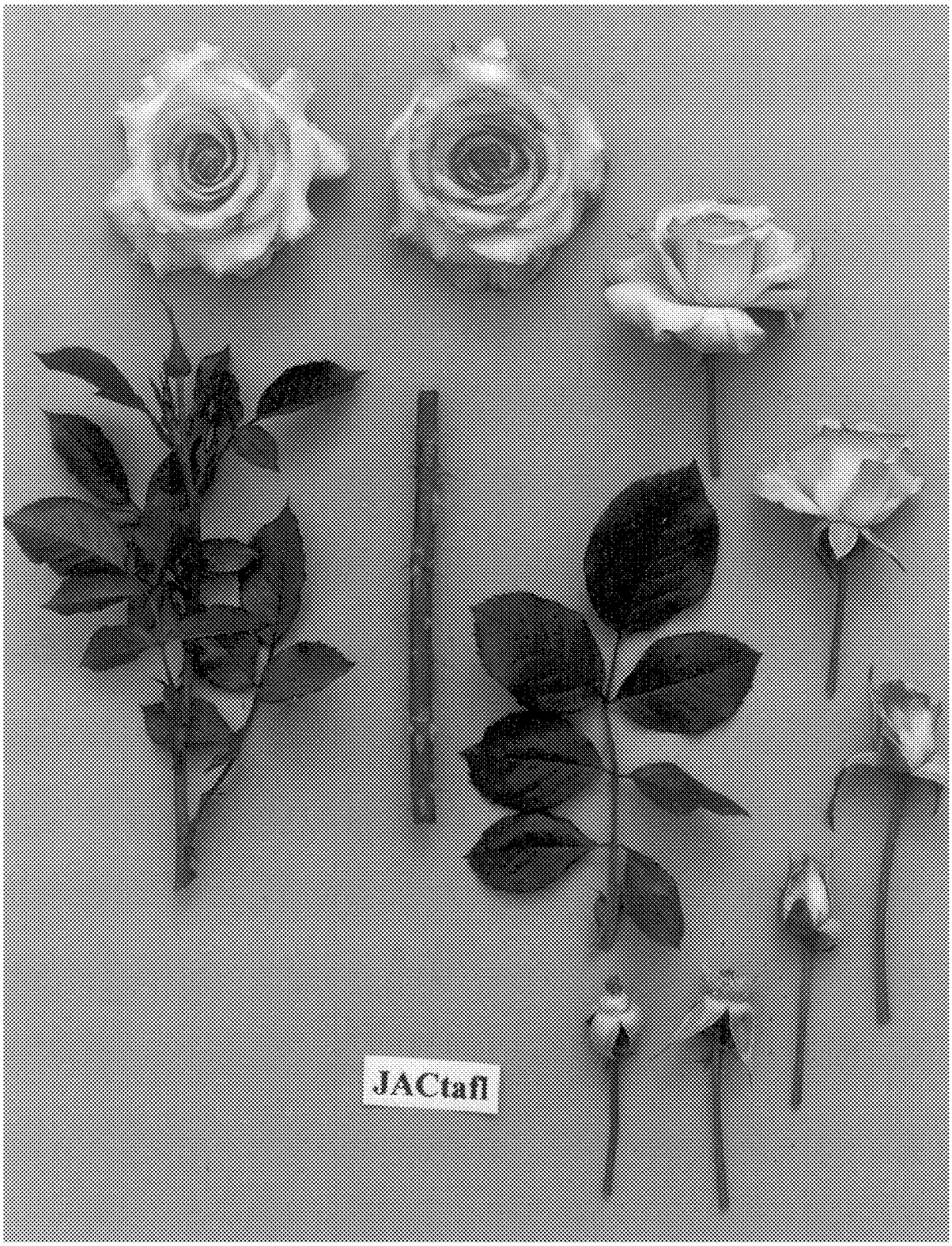
JACtaff